(12) United States Patent
Suh (10) Patent No.: US 6,520,931 B2
(45) Date of Patent: Feb. 18, 2003

(54) MEDICAL INSTRUMENT (75) Inventor: Jeong-Joo Suh, Seoul (KR)

(73) Assignee: G-Intek Co., Ltd., Seoul (KR)

( * ) Notice: Subject to any disclaimer, the term of this patent is extended or adjusted under 35 U.S.C. 154(b) by 113 days.

(21) Appl. No.: 09/759,410

(22) Filed: Jan. 12, 2001

(65) Prior Publication Data
US 2002/0022797 A1 Feb. 21, 2002

(30) Foreign Application Priority Data
Aug. 17, 2000 (KR) .............................. 00-47553

(51) Int. Cl.$^7$ ................................ A61M 1/06
(52) U.S. Cl. ..................... 604/73; 604/48; 604/540; 604/94.01; 604/118
(58) Field of Search .................... 604/48, 73, 289, 604/315, 317, 319–321, 540, 94.01, 99.04, 118

(56) References Cited

U.S. PATENT DOCUMENTS

| | | | | |
|---|---|---|---|---|
| 2,511,973 A | * | 6/1950 | Sierra, Jr. ................ | 604/94.01 |
| 3,783,867 A | * | 1/1974 | Summersby et al. ....... | 604/118 |
| 4,493,695 A | * | 1/1985 | Cook ........................ | 604/317 |
| 6,135,980 A | * | 10/2000 | Vu ............................ | 604/73 |

* cited by examiner

Primary Examiner—J. Casimer Jacyna
(74) Attorney, Agent, or Firm—Christie, Parker & Hale, LLP (57) ABSTRACT A medical instrument includes a case formed with a receiving space, a motor mounted in the case as a driving source which is driven by a battery, a power transmission element for converting a rotational motion of the motor to a linear motion, a pressure element connected to the power transmission element for inhaling and discharging ambient air so as to generate a suction force or discharging force of a predetermined pressure, a suction/discharge element integrally coupled with the pressure element and having an inlet for allowing an air to be inspired into the pressure element and an outlet for allowing the inspired air to be discharged from the pressure element to the outside, a power switch mounted an external surface of the case for controlling operations of the motor. Moreover, either of device or an injection device is detachably mounted to the main body of the medical instrument in communication with the inlet or the outlet of the suction/discharge element.

21 Claims, 9 Drawing Sheets

MEDICAL INSTRUMENT

CROSS-REFERENCE TO RELATED APPLICATION

This application claims priority of Korea patent Application No. 2000-47553, filed on Aug. 17, 2000.

BACKGROUND OF THE INVENTION (a) Field of the Invention

The present invention relates to a medical instrument, an more particularly, to a medical instrument to be used as a nasal aspirator or a rhinitis treatment instrument which may remove mucus by inhaling or strongly spraying fine granule type therapeutic medicines into a respiratory organ or a nasal cavity by detachably incorporating an aspirator or an injector in a single main body of the medical instrument.

(b) Description of the Related Art

In general, the moderns are highly subject to a common cold or rhinitis or other respiratory diseases due to the difference of temperature caused by seasonal variations, and increase of environmental pollution and air pollution.

In particular, infants and small children have low resistance to diseases and low ability to regulate body temperature by themselves, thus being subject to respiratory illness like a common cold caused by a variety of respiratory viruses, specially in winter times.

With the common cold, symptoms of nasal discharge, and nasal congestion/blockage usually commence in the early stage of illness. In case of infants or small children, and if progress to severity, dyspnea may be caused to infants or small children, which are potentially serious and even fatal disease. Even in case of adults, not only normal breathing becomes impossible causing inconvenience in activities but also diseases like rhinitis or empyemas may be resulted in.

To remove the blockage and obstruction from the nasal passage, tissue paper or swab is employed.

Recently, it has been proposed to remove the mucus by using a nasal aspirator that inhales mucus by using a motor power.

In the rhinitis referred to inflammation generated in a nasal mucus membrane in nose of the respiratory organ of a human body, viral rhinitis and allergic rhinitis are most popular. If a person is infected with the rhinitis, breathing becomes difficult and is accompanied with symptoms like headache or decline of attentiveness causing severer inconvenience.

Such a rhinitis patent may lighten the common cold or allergic rhinitis symptoms by inhaling or repeatedly flowing vapor of proper temperature into the nasal cavity.

As a medical instrument for lightening or curing the rhinitis symptoms, an ultrasonic spray type medical instrument for spraying a smallized granular vapor type therapeutic medicines or saline solution by using ultrasonic waves, and a compression air spray type medical instrument for spaying vapor generated by heating the therapeutic medicines or the saline solution at a predetermined temperature by using compressed air have been proposed.

The compression air spray type has been more widely used because of the higher therapeutic effect than the ultrasonic spraying type since the therapeutic medicines are more finely and strongly sprayed by using a motor power.

However, such a conventional nasal suction apparatus or rhinitis treatment instrument still has following drawbacks.

First, the conventional nasal suction apparatus or rhinitis treatment instrument is manufactured as a separate product to perform either one function to inhale mucus or to spray therapeutic medicines, and no further instrument for carrying out both of the two functions has been proposed.

Second, if it is necessary that both of the mucus inhaling and the treatment of the rhinitis should be performed, users should purchase two separate instruments respectively, which accordingly burdens the users with heavy expenses.

Both the foregoing general description and the following Detailed Description are exemplary and are intended to provide further explanation of the invention as claimed.

SUMMARY OF THE INVENTION

Therefore, the present invention is derived to resolve the disadvantages or problems of the prior art and it is an object of the present invention to provide a medical instrument to be used as a nasal aspirator or a rhinitis treatment instrument which may remove mucus by inhaling or strongly spraying fine granule type therapeutic medicines into a respiratory organ or a nasal cavity by detachably incorporating an aspirator or an injector in a single main body of the medical instrument.

To accomplish the above object of the present invention, there is provided a medical instrument including a case forming a shape of a main body of the medical instrument and having a receiving space, a motor mounted in the case as a driving source which is driven by a battery, a power transmission means for converting a rotational motion of the motor to a linear motion, a pressure means connected to the power transmission means for inhaling and discharging ambient air so as to generate a suction force or discharging force of a predetermined pressure, a suction/discharge means integrally coupled with the pressure means and having an inlet for allowing an air to be inspired into the pressure means and an outlet for allowing the inspired air to be discharged from the pressure means to the outside, and a power switch mounted an external surface of the case for controlling operations of the motor, wherein either of and a suction device or an injection device is detachably mounted to the medical instrument in communication with the inlet or outlet of the suction/discharge means.

The suction device is incorporated to perform a function as a nasal aspirator which inhales mucus by a suction force generated by an operation of the pressure means, and the injection device is incorporated to perform a function as a rhinitis treatment instrument by spraying fluid such as medicine by a discharge force generated by an operation of the pressure means.

The injection device is provided with an intermittent injection means in a main body for continuous injection of the fluid with a predetermined time interval, when the injection device is in use.

BRIEF DESCRIPTION OF THE DRAWINGS

The accompanying drawings provide a further understanding of the invention and, together with the Detailed Description, explain the principles of the invention. In the drawings.

DETAILED DESCRIPTION OF THE PREFERRED EMBODIMENTS

The present invention will be explained in more detail with reference to the attached drawings.

Figure 1:
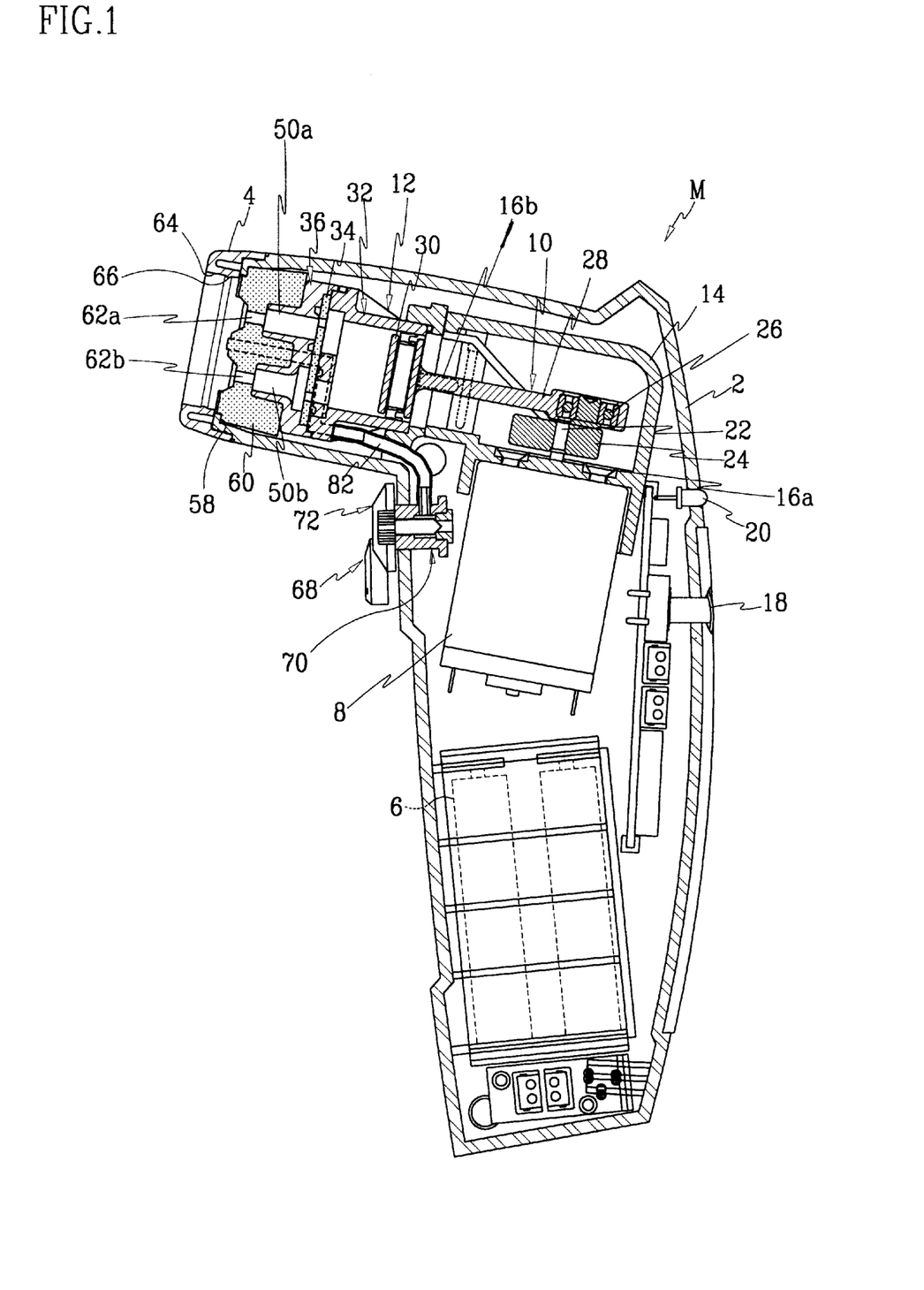
FIG. 1 is a section view illustrating a medical instrument according to the present invention.

FIG. 1 is a side section view illustrating a main body of a medical instrument according to the present invention. In FIG. 1, reference symbol 2 represents a case, which forms a shape of a main body M of the medical instrument and mounted with various parts.

The case 2, which is bent approximately perpendicularly for the sake of convenience of use of the medical instrument, has an internal space for accommodating a variety of parts and covered with a cap 4 at a front end part, which is detachably coupled with the case 2.

The case 2 accommodates a battery 6, a motor 8 as a driving source which is driven by a power supplied from the battery 6, a power transmission means 10 which receives the driving force from the motor 8 and converts a rotational motion to a linear motion, and a pressure means 12 which inhales and discharges ambient air in accordance with an actuation of the power transmission means 10 so as to generate a suction force having a predetermined pressure.

The motor 8 and the pressure means 12 are disposed approximately perpendicularly in a fixing part 14 in the case 2 and fixed and mounted by screws 16a and 16b.

Outside the case 2, a switch 18 is mounted for driving or stopping the motor 8 and an LED lamp 20 for displaying an operation state of the motor according to an operation of the switch 18.

The power transmission means 10 includes an eccentric cam 24 of which rotation center is fixed to a rotation axis 22 of the motor 8, and a bearing 26 coupled with an eccentric axis which is formed integrally with the eccentric cam 24 and extended outwardly from the cam 24, and a power transmission member 28 coupled outside the bearing 26 for converting an eccentric rotation motion of the eccentric cam 22 to a linear reciprocating motion.

The power transmission member 28 has an end installed perpendicularly to the rotation axis 22 of the motor 6 and the other end formed of a piston 30 which is connected to the pressure means 12.

Figure 2A:
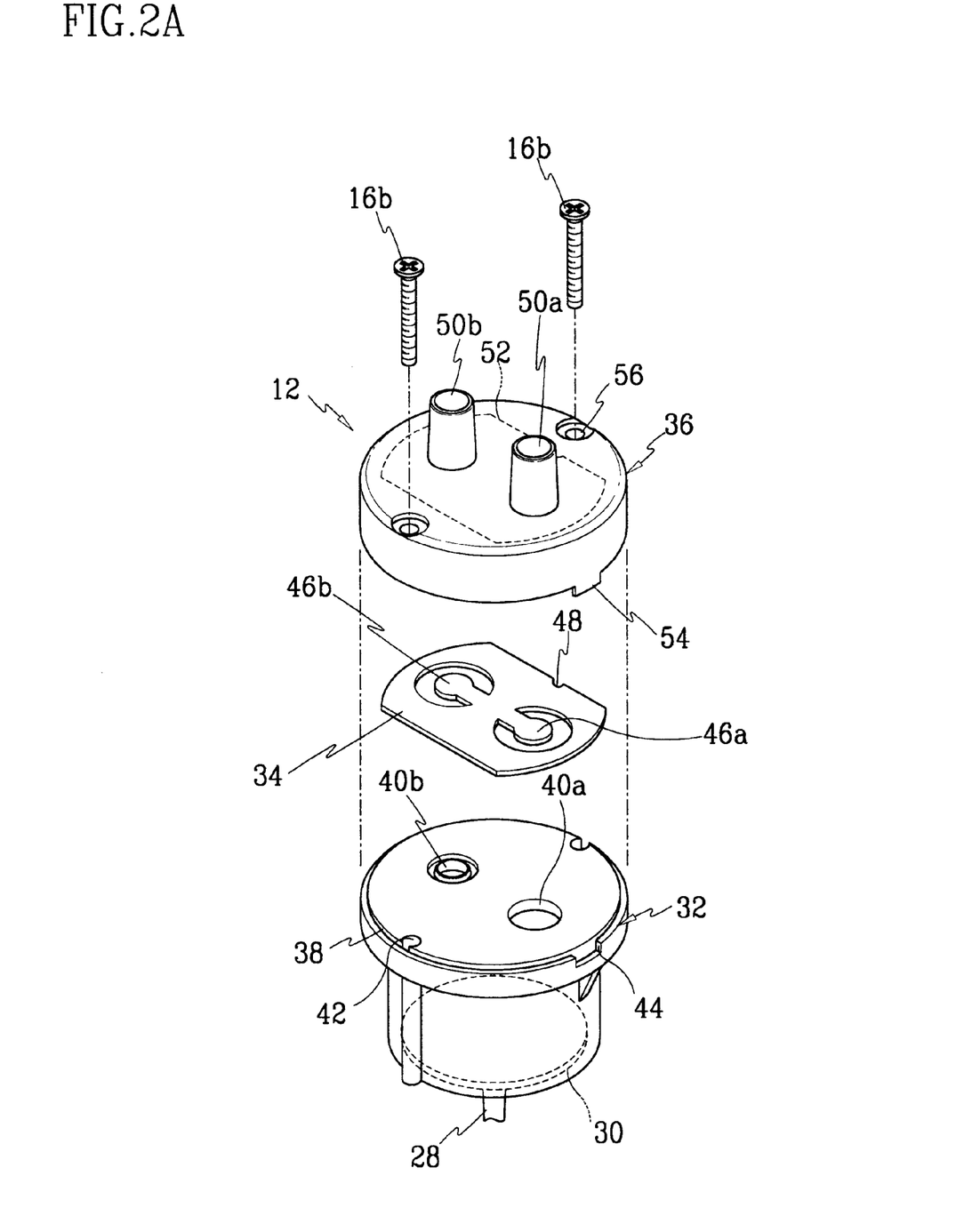
FIG. 2a and FIG. 2b are respectively an enlarged perspective view and assembled section view illustrating a pressure means employed by the present invention.
Figure 2B:
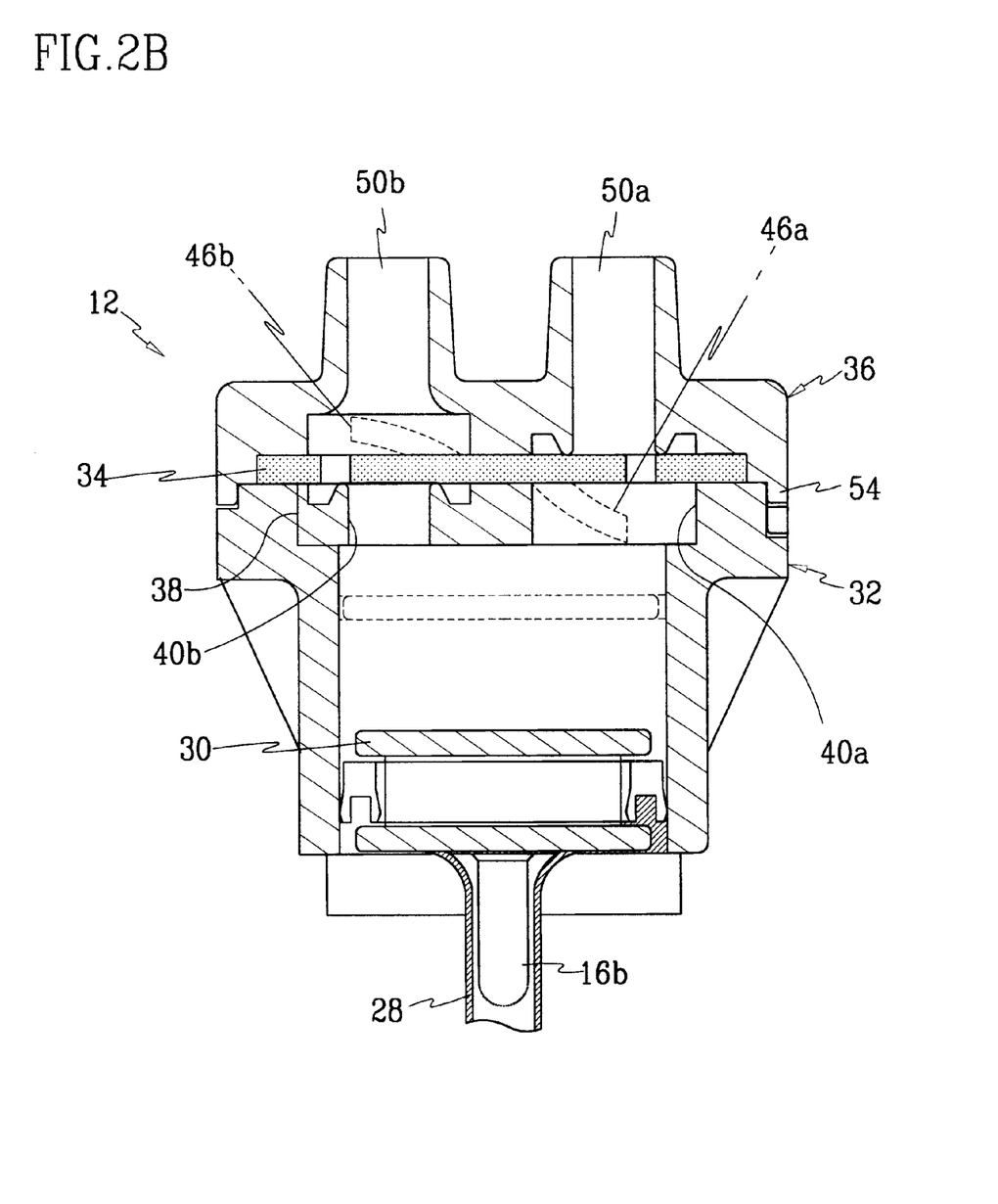

The pressure means 12 includes, as shown in FIG. 2, a cylinder 32 for allowing the piston 30 to be reciprocatingly moved inside thereof, a valve seat 34 positioned onto the cylinder 32, and a suction/discharge member 36 assembled into the cylinder 32 with the valve seat 34 disposed therebetween.

The cylinder 32 has a lower part which is opened for an insertion of the piston 32, and an upper part formed as a protruded shoulder part 38 having an inlet 40a and an outlet 40b at both sides for an air suction/discharge into/from the cylinder 32 by a reciprocating movement of the piston 30, and longitudinal holes(42) formed at both sides of an outer periphery in perpendicular to the inlet 40a and the outlet 40b.

Further, the cylinder 32 has a groove 44 at one side of an upper part of the outer periphery for precisely securing the suction/discharge member 36.

The cylinder 32 has, preferably, an inner diameter, which is proper for maintaining a minimum clearance with the piston 30 for a linear movement of the piston 30.

The valve seat 34 is tightly fitted between an upper surface of the cylinder 32 and the suction/discharge member 36 so as to keep a sealing therebetween and serves as a check valve. The valve seat 34 is made of a thin rubber having a resilience and has a first open/shut part 46a and a second open/shut part 46b, of which a portion is cut away so as to thereby open/shut the inlet 40a and the outlet 40b formed at the cylinder 32 upon up-and-down movement of the piston 30.

The first open/shut part 46a is formed smaller than the inlet 40a and the second open/shut part 46b is formed in a sufficient size to shut the outlet 40b. The valve seat 34 is provided with a groove 48 for the mounting of the valve seat 34 in the suction/discharge member 36 in a predetermined position.

The suction/discharge member 36 is assembled to the cylinder 32 with the valve seat 34 therebetween by tightly inserting an outer periphery of a bottom surface in the shoulder part 38 of the cylinder 32, and has an inlet 50a for allowing an air to be inspired into the pressure means 12 and an outlet 50b for allowing the inspired air to be discharged from the pressure means 12 to the outside.

The inlet 50a and the outlet 50b have a bottom structure opposite to a top part structure of the inlet 40a and the outlet 40b of the cylinder 32.

The suction/discharge member 36 has a groove 52 at a bottom surface, of which a depth is smaller than a thickness of the valve seat 34, thereby being fitted by the valve seat 34. Accordingly, when the cylinder 32 and the suction/discharge member 36 are assembled together, the valve seat 34-disposed therebetween is secured in surface-contact at both sides so that complete air tightness may be maintained.

The suction/discharge member 36 has a protrusion 54 at the outer periphery of the bottom surface corresponding to the groove 44 formed at the cylinder 32. When the cylinder 32 is assembled with the suction/discharge member 36, the groove 44 is assembled with the protrusion 54 for maintaining the inlet 40a and the outlet 40b of the cylinder 32 on a same axial line with the inlet 50a and the outlet 50b of the suction/discharge member 36.

The suction/discharge member 36 is provided with longitudinal holes 56 on a same axial line with the holes 42 of the cylinder 32, so that the pressure means 12 is assembled and fixed with cylinder 32 by inserting a screw 16b through the holes 56 and 42 and fixing the screw 16b in the fixing part 14 in a screw-coupling manner.

The pressure means 12 is structured in that, if the piston 30, for example, moves downwardly to the cylinder 32, the first and second open/shut parts 46a, 46b of the valve seat 34 are resiliently deformed toward the inlet 40a and the outlet 40b by a suction force of air, wherein the first open/shut part 46a and the inlet 40a are bent inwardly and the inlet 40a is opened while the outlet 40b is blocked, thus allowing an ambient air to be inspired into the cylinder 32 through the opened inlet 40a.

To the contrary, if the piton 30 moves upwardly from the lowered position, the first and second open/shut parts 46a, 46b of the valve seat 34 are resiliently deformed toward the suction/discharge member 36, and the inlet 50a is blocked by the first open/shut part 46a while the outlet 50b is opened by the second open/shut part 46b, thus allowing the air inspired into the cylinder 32 to be discharged through the outlet 50b.

Repeated action of the above-described air suction and discharge during a short period of time permits the pressure means 12 to generate a suction force or a repulsive force having a predetermined pressure.

A sealing member 60 having a predetermined resilience is inserted between the suction/discharge member 36 of the pressure means 12 and a protrusion 58 formed at a front end of the case 2, and a cap 4 disposed at an outside of the sealing member 60 is coupled to the case 2.

The sealing member 60 is for maintaining a tight sealing between the main body M of the medical instrument and the suction device or the injection device described hereinafter upon assembly, and made of a silicon or rubber having a predetermined resilience.

The sealing member 60 has an inlet 62a and an outlet 62b communicated with the inlet 50a and the outlet 50b of the suction/discharge member 36.

The cap 4 has a center portion thereof constituted by a cavity 64 having inner walls, and a protrusion 66 is formed in circumferential direction of the inner wall of the cavity 64 for an assembly with the suction device or the injection device.

Further, the medical instrument according to the above embodiment of the present invention is mounted with an intermittent injection means 68 in the main body for continuous injection of the fluid with a predetermined time interval as selected by a user, when the injection device described hereinafter is in use.

Figure 3A:
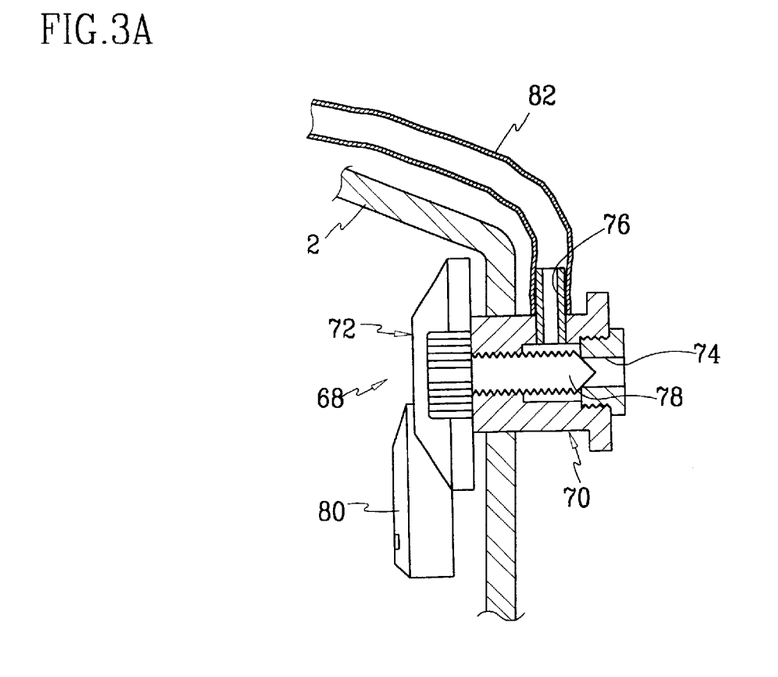
FIG. 3a and FIG. 3b are respectively enlarged section views illustrating an air introducing means employed by the present invention.
Figure 3B:
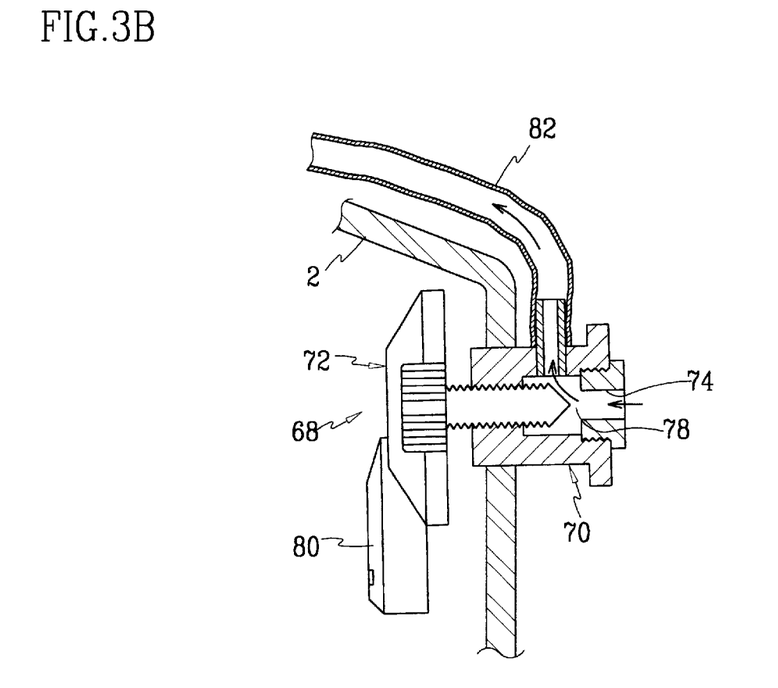

The intermittent injection means 68 includes, as shown in FIG. 3, an air introducing part 70 fixed in the case 2 for inhaling or discharging air, and a control part 72 connected to the air introducing part 70 for controlling an amount of fluid injection by controlling an amount of air to be inhaled into the air introducing part 70.

The air introducing part 70 has an opened part 74 at one side, of which central longitudinal part is formed as a female screw part in a center, and an air inlet 76 perpendicular to the opened part 74.

The control part 72 has an open/shut part 78 formed with a male screw part corresponding to the female screw part of the air introducing part 70 so as to control an opening/shutting degree of the opened part 74 by a to-and-fro movement due to rotation, and a lever 80 disposed outside the case 2, being coupled with the open/shut part 78.

The intermittent injection means 68 is structured in that, if the lever 80 rotates in one direction, the open/shut part 78 moves toward the opened part 74, thereby shutting the opened part 74 as shown in FIG. 3a, while if the lever 80 rotates in a reverse direction, the open/shut part 78 opens the opened part 74, thereby introducing ambient air into the air inlet 76 via the opened part 74.

The air inlet is connected to a tubular passage 82 extended to a front end of the sealing member 60.

The medical instrument is provided in the main body M with a suction device I and an injection device S which are detachably coupled to the main body and communicated with the inlet 50a or outlet 50b of the suction/discharge member 36.

The suction device I performs a function as a nasal aspirator which inhales nasal mucous by a suction force generated by the actuation of the pressure means 12, and the injection device S performs a function as a rhinitis treatment instrument which injects fluid such as medicines by a repulsive force generated by the pressure means 12.

Figure 4:
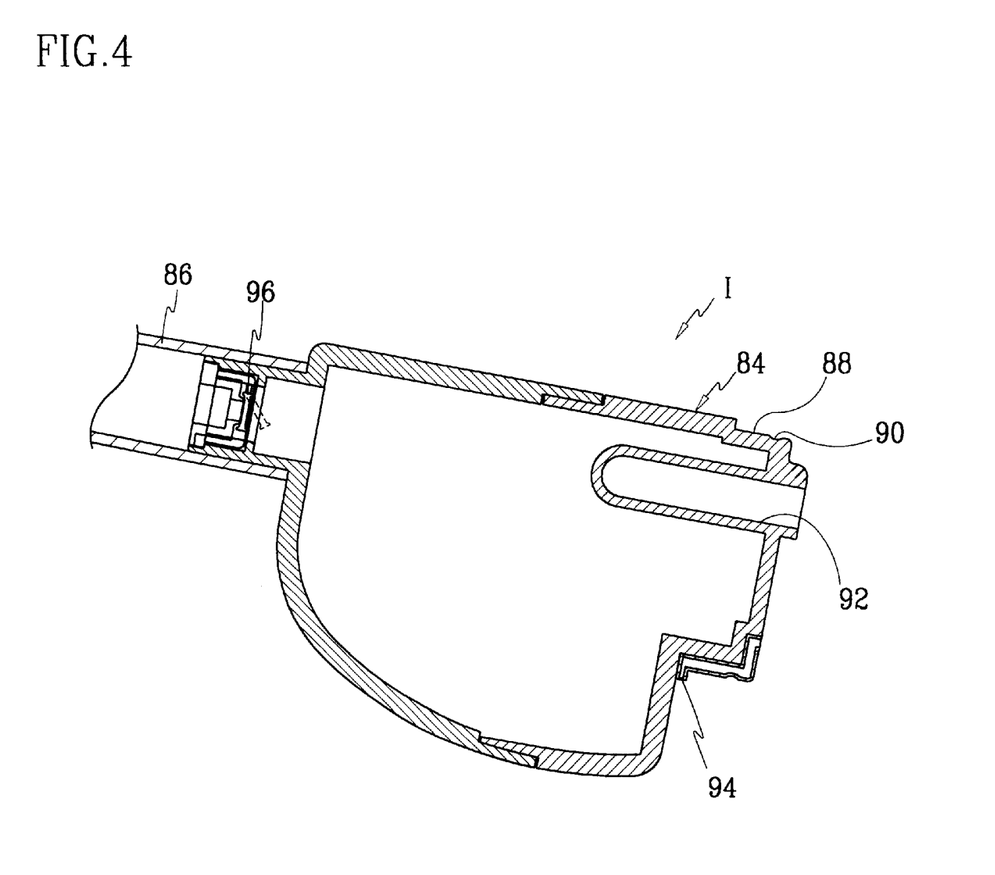
FIG. 4 is an enlarged section view illustrating a suction device employed by the medical instrument according to the present invention.
Figure 7:
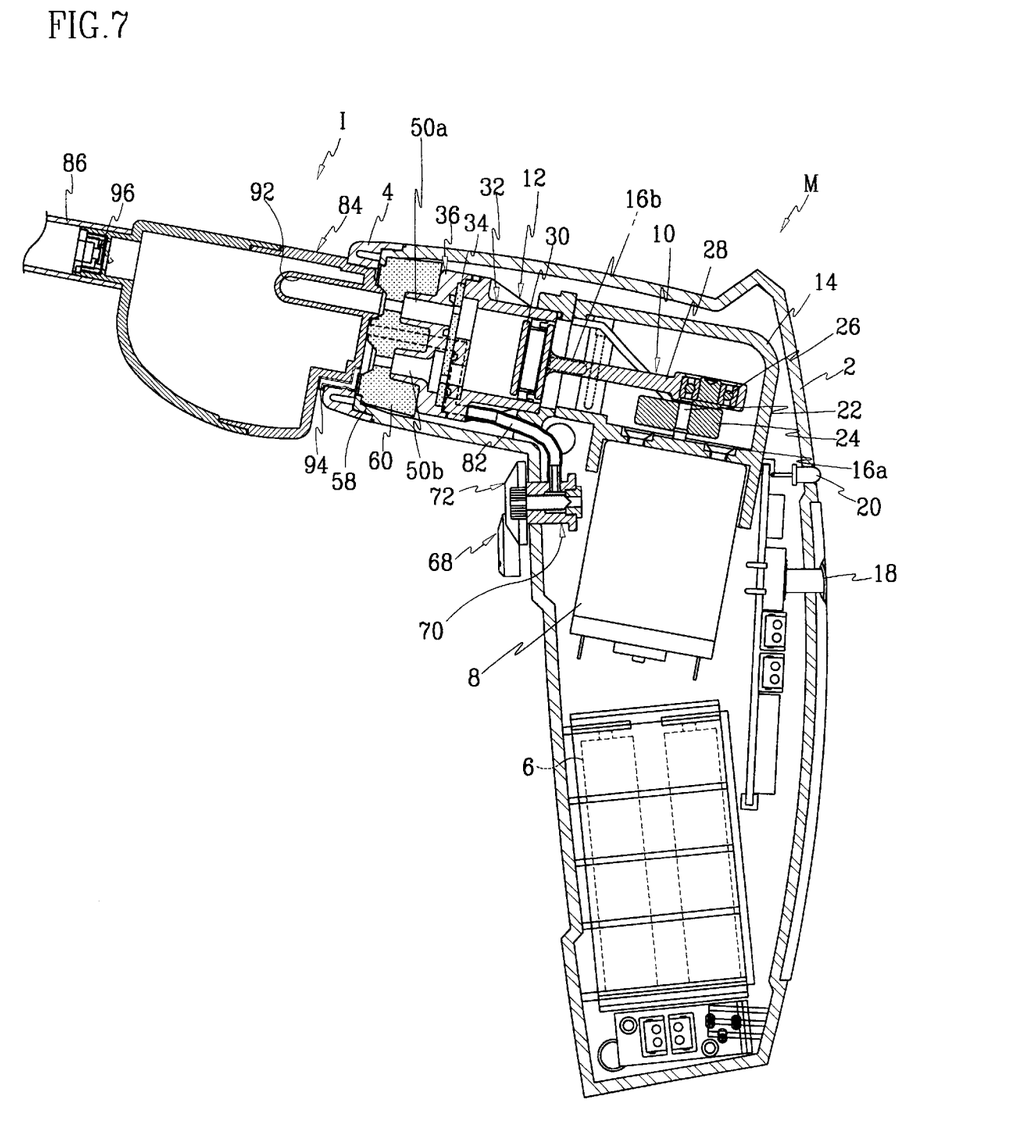
FIG. 7 is a section view illustrating an operation state of the medical instrument according to the present invention by mounting the suction device.

The suction device I includes, as shown in FIG. 4 and FIG. 7, a nasal mucus container detachably coupled to the main body M of the medical instrument for inspiring nasal mucus and collecting the inspired nasal mucus.

The nasal mucus container has a main body 84 detachably fitted and a nasal mucus suction hole 86 coupled at a front end of the main body 84 which initially inspires the nasal mucus.

The main body 84 of the nasal mucus container has an insertion part 88, which is detachably coupled, at an interior of the cavity 64 of the cap 4, thereby coupled with the main body M of the medical instrument. The insertion part 88 has a groove 90 corresponding to the protrusion 66 formed on the inner walls of the cavity 64, thereby coupling the suction device I with the main body M of the medical instrument tightly.

The nasal mucus suction hole 86 is preferably made of flexible materials such as silicon and rubber, since the nasal mucus aspirator is inserted into the nose.

The main body 84 of the nasal mucus container is formed with an air suction tube 92, which is extended from the main body, near the insertion part 88. The air suction tube 92 is in close contact and communication with a front end of the inlet 62a, which is communicated with the inlet 50a of the suction/discharge member 36.

The insertion part 88 of the main body 84 is provided at one side with a discharge tube passage 94 in communication with the outlet 62b for exhausting air discharged by the actuation of the pressure means 12.

The main body 84 of the nasal container is provided with a discharge tube passage 94 formed with an outlet 62b at one side of the insertion part 88, which discharges air discharged by the actuation of the pressure means 12 to the outside.

The main body 84 of the nasal mucus container is provided with a backflow prevention valve 96 for preventing the nasal mucus inspired into the main body 84 of the nasal mucus container from being flowed back toward the nasal mucus suction hole 86.

The backflow prevention valve 96 is made of a resilient material like a rubber, and is blocked normally and opened at a lower portion thereof during nasal suction operation, as shown in a dotted line of FIG. 4, allowing the nasal mucus to be inspired into the main body 84 of the nasal mucus container.

Even though the front end portion of the nasal mucus suction hole 86 is positioned downwardly, the nasal mucus inspired into the main body 84 of the nasal mucus container is closed therein due to the tare of the backflow prevention valve 96 and self-resilience so that the inspired nasal mucus can not flow to the outside.

Figure 5:
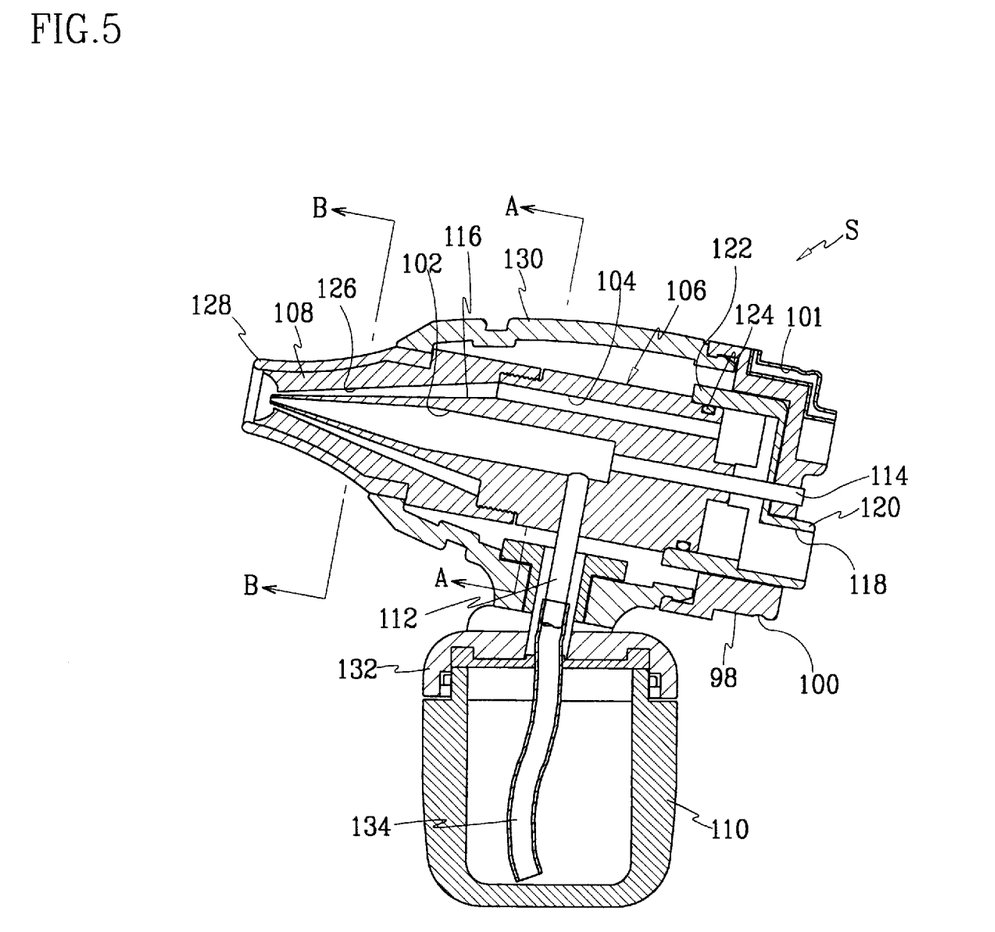
FIG. 5 is an enlarged injection device employed by the medical instrument according to the present invention.
Figure 8:
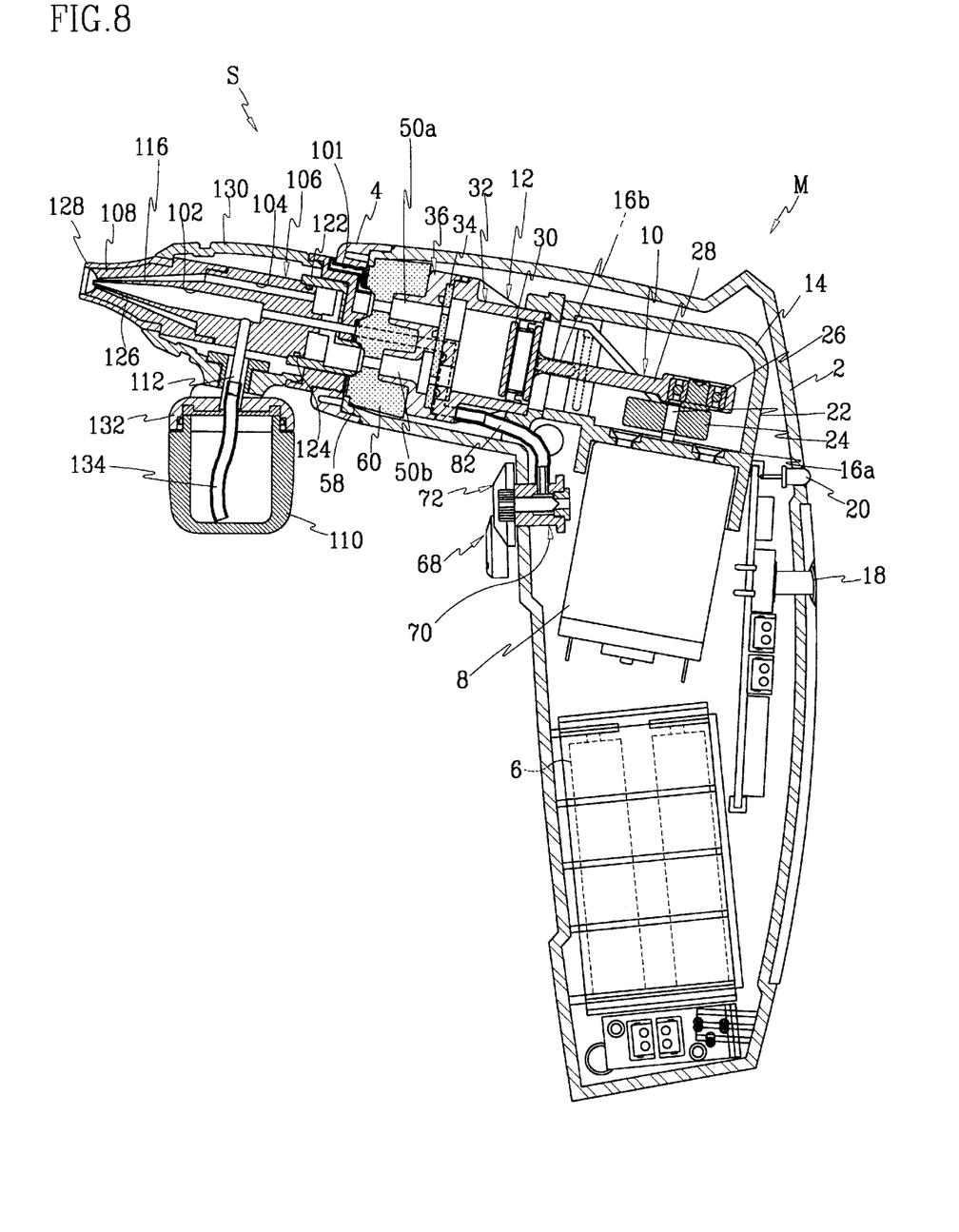
FIG. 8 is a section view illustrating an operation state of the medical instrument according to the present invention by mounting the injection device.

The injection device S is, as shown in FIG. 5 and FIG. 8, to be a fluid injection device, which is detachably coupled with the main body M of the medical instrument, for spraying saline water or medicines into the nasal cavity of rhinitis patents by the actuation of the pressure means 12.

The fluid injection device has an insertion part 98 to be coupled inwardly with the cavity 64 of the cap 4 coupled at a front end of the main body M of the medical instrument, and the insertion part 98 is formed with a groove 100 corresponding to the protrusion 66 formed on the inner walls of the cavity 64 for the tight coupling between the main body M of the medical instrument and the injection device S.

The insertion part 98 has a suction tube passage 101 for supplying ambient air into the inlet 62a formed on the main body M of the medical instrument.

The fluid injection device includes a main body 106 having a fluid channel 102 penetrated in the middle portion longitudinally for flowing fluid along, and air channels 104 formed outside of the fluid channel 102 for discharging the fluid by reducing an internal pressure of the fluid channel 102 by the force of air generated by the pressure means 12 of the main body M of the medical instrument, a nozzle 108 coupled with an outside of a front end part of the main body 106 of the injection device with a certain distance, a fluid supply tube 112 connected to the fluid channel 102 at one side and to a container 110 filled with fluid at the other end, and an air supply tube 114 connected to the fluid channel 102 for mixing and introducing ambient air into the fluid channel by a predetermined interval when injecting the fluid.

The fluid channel 102 has a front end portion of which diameter becomes gradually narrower for a stronger injection of the fluid. When the injection device S is coupled with the main body M of the medical instrument, the front end part of the fluid channel 102 becomes communicated with the air supply tube 114, which is formed at a rear part of the fluid channel 102, and an extension tube passage 82, which is extended from the intermittent injection means 68.

The main body 106 of the injection device has a tapered part 116 at a front part, and a rear part coupled via a packing 124 with jaw 122 of a connecting part 120 which has an air inlet 118, wherein compression air generated in the pressure means 12 of the main body M of the medical instrument may be supplied to the main body 106 of the injection device via the connection part 120.

Figure 6A:
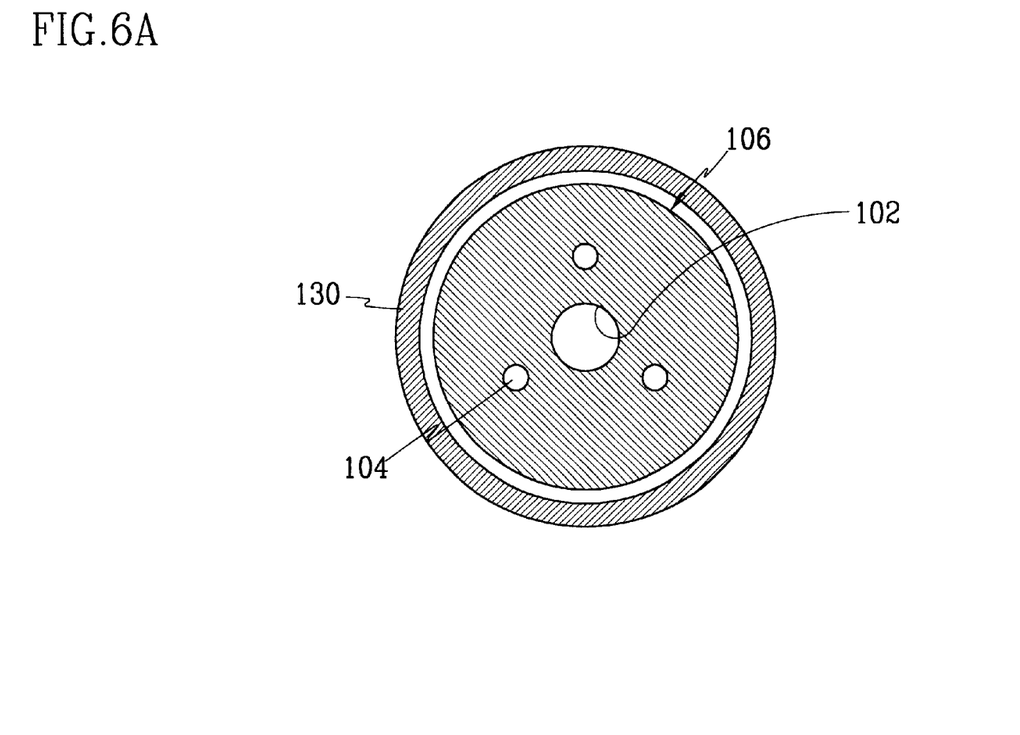
FIG. 6a is an enlarged section view taken along A—A line of FIG. 5.

The air inlet 118 is communicating with the air channels 104 formed on the main body 106 of the injection device, wherein a plurality of the air channels 104 are punched on the fluid channel 102 along an outer periphery thereof with a predetermined interval, the fluid channel 102 being formed in a longitudinal direction of the central part of the main body 106 of the injection device, as shown in FIG. 6a.

Figure 6B:
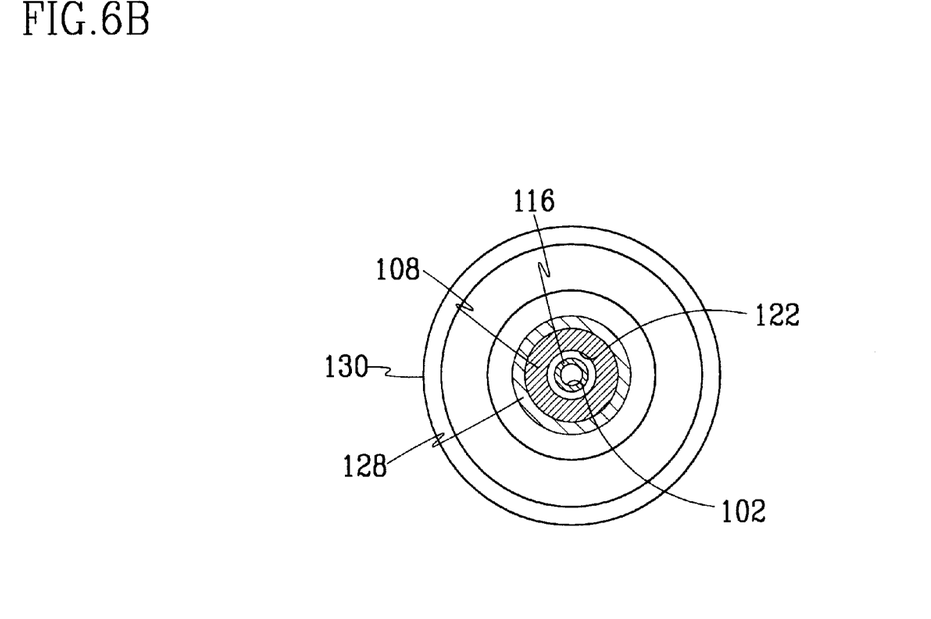
FIG. 6b is an enlarged section view taken along B—B line of FIG. 5.

As shown in FIG. 6b, the nozzle 108 and the tapered part 116 of the main body 106 of the injection device are coupled at an outside of the front end part of the main body 106 with a predetermined distance, so that a cavity 126 is formed between the nozzle 108 and the tapered part 116, through which the cavity 126 is communicated with the air channels 104 and the compression air may be discharged from the nozzle 108 via the main body 106 of the injection device.

An end part of the nozzle 108 is positioned at a withdrawn position than an end part of the main body 106 of the injection device and, by this configuration, the compression air discharged via the cavity 126 is prevented from being introduced toward the fluid channel 102.

An outside of the nozzle 108 is covered by a nozzle cover 128, wherein the nozzle cover 128 is supported by the nozzle 108 at one side and accommodates a part of the connecting part 120 and the main body 106 of the injection device.

A lid 132 is detachably coupled with the container 110 for covering an upper part of the container 110 at a lower part of the fluid supply tube 112.

An extension part 134 is extended from a lower end part of the fluid supply tube 112 to a lower part in the container 110 for supplying fluid filled in the container 110 to the fluid supply tube 112.

According to the above embodiment of the present invention, the injection device S is provided to the main body M of the medical instrument and may be connected with the intermittent injection means 68 as desired for introducing ambient air through the fluid channel 102 and continuously spraying the fluid with a predetermined interval.

The intermittent injection means 68 is communicated with the air supply tube 114 formed in the injection device S via the extension tube passage 82 and communicated with the main body M of the medical instrument as coupled therewith.

To use thus-configured medical instrument as a nasal aspirator, the suction device I is coupled to the main body M of the medical instrument and a switch 18 is turned on.

Thus, a power from the battery 6 is transmitted to the motor 8 so as to drive the motor 8, the eccentric cam 24 coupled to the rotation shaft 22 of the motor 8 rotates, and the power transmission member 28 of the power transmission means 10 coupled to be rotatable at the bearing 26 coupled outside the eccentric cam 24 converts the rotation motion into the linear motion.

Subsequently, the piston 40 arranged at a side of the power transmission member 28 moves reciprocatingly within the cylinder 32 of the pressure means 12 by the actuation of the power transmission member 28.

If the piston 30 moves downwardly, the first and second open/shut parts 46a, 46b of the valve seat 34 is resiliently deformed toward the inlet 40a and the outlet 40b by the suction force of air, the first open/shut part 46a is bent into the inlet 40a, opening the inlet 40a, and the second open/shut part 46b shuts the outlet 40b, thus allowing ambient air to be inspired into the cylinder 32 through the nasal mucus suction hole 86, the air suction tube 92, the inlet 50a of the pressure means 12 and the open inlet 40a in sequence.

To the contrary, if the piston 30 again moves upwardly from the lowered position, the first and second open/shut parts 46a, 46b of the valve seat 34 are lifted toward the suction/discharge member 36, wherein the first open/shut part 46a shuts the inlet 50a while the second open/shut part 46b opens the outlet 50b, thus allowing the air inspired into the cylinder 32 to be discharged to the outside though the discharge tube passage 94 of the suction device 1.

Repeated action of the above-described air suction and discharge during a short period of time permits the pressure means 12 to generate a suction force of a uniform pressure. Under the circumstances, the nasal mucus is inspired by inserting the nasal mucus suction hole 86 coupled at the front end of the suction device I into a nose of a person who wants to remove his nasal mucus.

The nasal mucus in the nose is inspired along the nasal mucus suction hole 86 and stays in the main body 84 of the nasal mucus container.

Air inspired with the nasal mucus into the main body 84 of the nasal mucus container is introduced into the pressure means 12 through the air suction tube 92, the inlet 62a and the inlet 50a, and discharged from the air discharge tube 94 via the outlet 50b and the outlet 62b.

As the power switch 18 is turned off, the rotation of the motor 8 is stopped and accordingly the operation of the medical instrument is stopped.

If a predetermined amount of nasal mucus is inspired into the main body 84 of the nasal mucus container, the suction device I is separated from the main body M of the medical instrument, the main body 84 of the nasal mucus container 84 is separated from the suction device I to empty, and then the above main body of the nasal mucus container and the suction device are assembled again for future use.

In order the use the medical instrument as a rhinitis treatment instrument, the suction device I coupled to the main body M of the medical instrument is separated therefrom and the injection device S as shown in FIG. 5 is coupled, wherein the fluid is sprayed by using the repulsive force of air generated by the pressure means 12.

In order to use the fluid injection device, the container 110 is filled with a fluid to use and coupled to the main body M of the medical instrument in such a manner that the air inlet 118 of the injection device S is communicated with the outlet of the main body M of the medical instrument.

Next, if the switch 18 is turned on, the piston 30 moves reciprocatingly in the cylinder 32 by the actuation of the pressure means 12 as described hereinabove, so that ambient air is introduced into the cylinder 32 via the suction tube passage 101 formed in the injection device S, the inlet 62a and the inlet 50a in sequence, and the inspired ambient air is discharged via the outlet 50b and the outlet 62b.

Then, the compression air is supplied to the injection device S via the air inlet 118 connected to the outlet 62b, and discharged to the outside via the cavity 126 of the nozzle 108 along the air channel 104 of the main body 106 of the injection device.

If it is assumed that, as shown in FIG. 3a, the opened part 74 of the air introducing part 70 mounted in the main body M of the medical instrument is blocked by the open/shut part 78, an internal pressure of the container 110 filled with the fluid decreases as the velocity of the moving compression air becomes increases in accordance with the Bernoulli's hydrodynamics theorem. Therefore, the fluid in the container 110 is sprayed outside together with the compression air while moving along the fluid channel 102 via the extension part 134 and the fluid supply tube 112, and such spraying is continued as far as the supply of the compression air is continued.

Under the circumstances, if the open/shut part 78 which is blocking the opened part 74 is moved outwardly by rotating the lever 80 of the intermittent injection means 68 as shown in FIG. 3b, the opened part 74 is opened and ambient air is introduced into the air supply tube 114 via the air inlet 76 and the extension tube passage 82.

Since a pressure of the air introduced into the air supply tube 114 (atmospheric pressure) is larger than a pressure of the fluid conveyed along the fluid supply tube 112, the flow of fluid conveyed along the fluid supply tube 112 is blocked and ambient air flows in the fluid channel 102.

By the operation described as above, the spraying of the fluid is not performed but the ambient air is sprayed.

If the air is sprayed as above, the atmospheric pressure of the fluid channel 102 decreases below the pressure of the fluid, so that the fluid to which the atmospheric pressure is applied is drawn out into the fluid supply tube 112, thereby blocking the supply of air.

As the fluid is again sprayed by the above operation, the atmospheric pressure is introduced into the fluid channel 102 again, stopping the spraying of the fluid.

Therefore, under the state that the compression air is continuously supplied and the opened part 74 is open, the intermittent injection is performed by repeating the spraying of fluid—the stopping the fluid spraying—the spraying of fluid.

The spraying of fluid and the stopping of the fluid spraying are performed by the introduction of air so that the time period of the intermittent injection is determined by a degree of opening of the opened part 74.

As described hereinabove, the medical instrument according to the present invention may be used as a nasal mucus aspirator or a rhinitis treatment instrument by simply coupling the suction device or the injection device to a single main body for inspiring nasal mucus or strongly spraying therapeutic medicines of a fine granule type into the nasal cavity, thereby expanding the utility of the medical instrument and improving the convenience of use.

Further, the carrying and maintaining of the medical instrument is convenient by performing the functions as the nasal mucus aspirator and the rhinitis treatment instrument by simply changing the suction device or the injection device coupled to the single main body with the other one, thereby reducing the consumers' burden in comparison with the case purchasing both of the separate products.

It will be apparent to those skilled in the art that various modifications and variations can be made to the device of the present invention without departing from the spirit and scope of the invention. The present invention covers the modifications and variations of this invention provided they come within the scope of the appended claims and their equivalents.

What is claimed is:

1. A medical instrument comprising:
    a case forming a shape of a main body of the medical instrument and having a receiving space;
    a motor mounted in the case as a driving source, which is driven by a battery;
    a power transmission means for converting a rotational motion of the motor to a linear motion, wherein the power transmission means comprises an eccentric cam of which a rotation center is fixedly mounted on a rotation shaft of the motor, a bearing coupled to an eccentric shaft and integrally formed with the eccentric cam, and a power transmission member coupled outside the bearing for converting an eccentric rotational motion of the eccentric cam to a linear reciprocating motion;
    a pressure means connected to the power transmission means for inhaling and discharging ambient air so as to generate a suction force or discharging force of a predetermined pressure;
    a suction/discharge means integrally coupled with the pressure means and having an inlet for allowing an air to be inspired into the pressure means and an outlet for allowing the inspired air to be discharged from the pressure means to the outside; and
    a power switch mounted an external surface of the case for controlling operations of the motor;
    wherein either of a suction device or an injection device is detachably mounted to the medical instrument in communication with the inlet or outlet of the suction/discharge means.

2. A medical instrument of claim 1, wherein the pressure means comprises a piston mounted at one side of the power transmission member, a cylinder for moving reciprocatingly in the piston, a valve seat positioned at an upper part of the cylinder, and a suction/discharge member assembled with the cylinder, the valve seat being interposed between the suction/discharge member and the cylinder.

3. A medical instrument of claim 1, wherein the suction device is detachably coupled to the main body, so that medical instrument serves as a nasal mucus aspirator by the suction force generated by the actuation of the pressure means.

4. A medical instrument of claim 3, wherein the suction device comprises a nasal mucus container to be detachably fitted and filled with inspired nasal mucus, and a nasal mucus suction hole coupled at a front end of the nasal mucus container for initiating the suction of the nasal mucus.

5. A medical instrument of claim 4, wherein the nasal mucus container has an insertion part detachably coupled with an interior part of a cavity formed in a front end of the medical instrument to be coupled with the medical instrument, and the insertion part is formed with a groove corresponding to a protrusion formed on inner walls of the cavity for tight coupling between the suction device and the medical instrument.

6. A medical instrument of claim 5, wherein the insertion part of the nasal mucus container is provided at one side with a discharge tube passage for discharging air to be discharged to the outside by the actuation of the pressure means.

7. A medical instrument of claim 1, further comprising:
an intermittent injection means for continuously injecting fluid with a predetermined time interval as selected by a user when the injection device is mounted to use.

8. A medical instrument of claim 7, wherein the intermittent injection means comprises an air introducing part, fixed to the case, having an opened part and an air inlet for performing the suction or discharge of air, and a control part screw-coupled movably in the air introducing part for controlling an amount of air to be introduced into the air introducing part to control fluid injection.

9. A medical instrument of claim 1, wherein the injection device is detachably coupled with the medical instrument for serving as a rhinitis treatment instrument by injecting a fluid such as therapeutic medicines by repulsive force generated by the actuation of the pressure means.

10. A medical instrument of claim 9, wherein the injection device comprises:
a main body having a fluid channel formed in the middle portion longitudinally for flowing fluid along, and air channels formed outside of the fluid channel for allowing the fluid discharged by reducing an internal pressure of the fluid channel by the force of air generated by the pressure means of the medical instrument;
a nozzle coupled with an outside of a front end part of the injection device with in a predetermined distance;
a fluid supply tube connected to the fluid channel at one side and to a container filled with a fluid at the other side; and
an air supply tube connected to the fluid channel and the intermittent injection means, in turn, for mixing and introducing ambient air into the fluid channel a predetermined time interval when injecting the fluid.

11. A medical instrument of claim 9, wherein the injection device has an insertion part to be coupled with a cap, the cap being coupled at a front end of the medical instrument and the insertion part is formed with a groove corresponding to the protrusion formed on the inner walls of the cap for tight coupling between the injection device and the medical instrument.

12. A medical instrument of claim 11, wherein the insertion part has a suction tube passage for supplying ambient air by the pressure means.

13. A medical instrument comprising:
a case forming a shape of a main body of the medical instrument and having a receiving space;
a motor mounted in the case as a driving source, which is driven by a battery;
a power transmission means for converting a rotational motion of the motor to a linear motion;
a pressure means connected to the power transmission means for inhaling and discharging ambient air so as to generate a suction force or discharging force of a predetermined pressure, wherein the pressure means comprises a piston mounted at one side of the power transmission member, a cylinder for moving reciprocatingly in the piston, a valve seat positioned at an upper part of the cylinder, and a suction/discharge member assembled with the cylinder, the valve seat being interposed between the suction/discharge member and the cylinder;
a suction/discharge means integrally coupled with the pressure means and having an inlet for allowing an air to be inspired into the pressure means and an outlet for allowing the inspired air to be discharged from the pressure means to the outside; and
a power switch mounted an external surface of the case for controlling operations of the motor;
wherein either of a suction device or an injection device is detachably mounted to the medical instrument in communication with the inlet or outlet of the suction/discharge means.

14. A medical instrument comprising:
a case forming a shape of a main body of the medical instrument and having a receiving space;
a motor mounted in the case as a driving source, which is driven by a battery;
a power transmission means for converting a rotational motion of the motor to a linear motion;
a pressure means connected to the power transmission means for inhaling and discharging ambient air so as to generate a suction force or discharging force of a predetermined pressure;
a suction/discharge means integrally coupled with the pressure means and having an inlet for allowing an air to be inspired into the pressure means and an outlet for allowing the inspired air to be discharged from the pressure means to the outside; and
a power switch mounted an external surface of the case for controlling operations of the motor;
wherein either of a suction device or an injection device is detachably mounted to the medical instrument in communication with the inlet or outlet of the suction/discharge means, wherein the suction device is detachably coupled to the main body, so that medical instrument serves as a nasal mucus aspirator by the suction force generated by the actuation of the pressure means, wherein the suction device comprises a nasal mucus container to be detachably fitted and filled with inspired nasal mucus, and a nasal mucus suction hole coupled at a front end of the nasal mucus container for initiating the suction of the nasal mucus, and wherein the nasal mucus container has an insertion part detachably coupled with an interior part of a cavity formed in a front end of the medical instrument to be coupled with the medical instrument, and the insertion part is formed with a groove corresponding to a protrusion formed on inner walls of the cavity for tight coupling between the suction device and the medical instrument.

15. A medical instrument of claim 14, wherein the insertion part of the nasal mucus container is provided at one side with a discharge tube passage for discharging air to be discharged to the outside by the actuation of the pressure means.

16. A medical instrument comprising:
   a case forming a shape of a main body of the medical instrument and having a receiving space;
   a motor mounted in the case as a driving source, which is driven by a battery;
   a power transmission means for converting a rotational motion of the motor to a linear motion;
   a pressure means connected to the power transmission means for inhaling and discharging ambient air so as to generate a suction force or discharging force of a predetermined pressure;
   a suction/discharge means integrally coupled with the pressure means and having an inlet for allowing an air to be inspired into the pressure means and an outlet for allowing the inspired air to be discharged from the pressure means to the outside;
   a power switch mounted an external surface of the case for controlling operations of the motor, wherein either of a suction device or an injection device is detachably mounted to the medical instrument in communication with the inlet or outlet of the suction/discharge means; and
   an intermittent injection means for continuously injecting fluid with a predetermined time interval as selected by a user when the injection device is mounted to use.

17. A medical instrument of claim 16, wherein the intermittent injection means comprises an air introducing part, fixed to the case, having an opened part and an air inlet for performing the suction or discharge of air, and a control part screw-coupled movably in the air introducing part for controlling an amount of air to be introduced into the air introducing part to control fluid injection.

18. A medical instrument comprising:
   a case forming a shape of a main body of the medical instrument and having a receiving space;
   a motor mounted in the case as a driving source, which is driven by a battery;
   a power transmission means for converting a rotational motion of the motor to a linear motion;a
   pressure means connected to the power transmission means for inhaling and discharging ambient air so as to generate a suction force or discharging force of a predetermined pressure;
   a suction/discharge means integrally coupled with the pressure means and having an inlet for allowing an air to be inspired into the pressure means and an outlet for allowing the inspired air to be discharged from the pressure means to the outside;
   a power switch mounted an external surface of the case for controlling operations of the motor, wherein either of a suction device or an injection device is detachably mounted to the medical instrument in communication with the inlet or outlet of the suction/discharge means, and wherein the injection device is detachably coupled with the medical instrument for serving as a rhinitis treatment instrument by injecting a fluid such as therapeutic medicines by repulsive force generated by the actuation of the pressure means.

19. A medical instrument of claim 18, wherein the injection device comprises:
   a main body having a fluid channel formed in the middle portion longitudinally for flowing fluid along, and air channels formed outside of the fluid channel for allowing the fluid discharged by reducing an internal pressure of the fluid channel by the force of air generated by the pressure means of the medical instrument;
   a nozzle coupled with an outside of a front end part of the injection device with in a predetermined distance;
   a fluid supply tube connected to the fluid channel at one side and to a container filled with a fluid at the other side; and
   an air supply tube connected to the fluid channel and the intermittent injection means, in turn, for mixing and introducing ambient air into the fluid channel a predetermined time interval when injecting the fluid.

20. A medical instrument of claim 18, wherein the injection device has an insertion part to be coupled with a cap, the cap being coupled at a front end of the medical instrument and the insertion part is formed with a groove corresponding to the protrusion formed on the inner walls of the cap for tight coupling between the injection device and the medical instrument.

21. A medical instrument of claim 20, wherein the insertion part has a suction tube passage for supplying ambient air by the pressure means.

* * * * *